US006891919B2

(12) United States Patent
Kresse et al.

(10) Patent No.: US 6,891,919 B2
(45) Date of Patent: May 10, 2005

(54) X-RAY TECHNIQUE-BASED NONINTRUSIVE INSPECTION APPARATUS HAVING AN ADJUSTABLE COLLIMATOR ASSEMBLY

(75) Inventors: David E. Kresse, Walnut Creek, CA (US); Andrew J. Banchieri, Newark, CA (US)

(73) Assignee: InVision Technologies, Inc., Newark, CA (US)

( * ) Notice: Subject to any disclaimer, the term of this patent is extended or adjusted under 35 U.S.C. 154(b) by 119 days.

(21) Appl. No.: 10/280,498

(22) Filed: Oct. 25, 2002

(65) Prior Publication Data

US 2004/0081274 A1 Apr. 29, 2004

(51) Int. Cl.[7] .............................................. G01N 23/00
(52) U.S. Cl. .............................. 378/19; 378/4; 378/151
(58) Field of Search ................................ 378/4, 19, 57, 378/58, 147, 150, 151

(56) References Cited

U.S. PATENT DOCUMENTS 6,487,267 B1 * 11/2002 Wolter ............................ 378/4

* cited by examiner

*Primary Examiner*—Craig E. Church
*Assistant Examiner*—Jurie Yun
(74) *Attorney, Agent, or Firm*—Blakely, Sokoloff, Taylor & Zafman; Stephen M. De Klerk

(57) ABSTRACT

An x-ray-based nonintrusive inspection apparatus has a collimator shield. An adjusting actuator is actuable to move the collimator shield between a pre-scanning position and a CT scanning position, in the pre-scanning position, the collimator shield exposing a smaller portion of a respective crystal to the x-rays than in the CT scanning position. A controller is connected to a gantry motor and the adjusting actuator. The controller controls the motor and the adjusting actuator such that the collimator shield is in the pre-scanning position when a gantry is stationary and in the CT scanning position when the gantry is rotating.

17 Claims, 4 Drawing Sheets

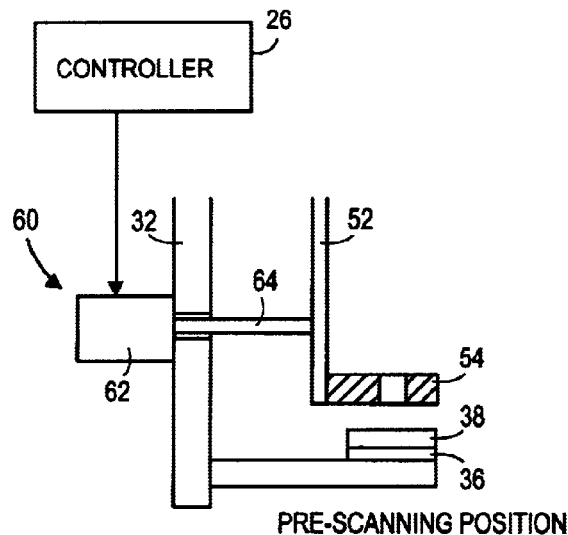
FIG. 4 PRE-SCANNING POSITION
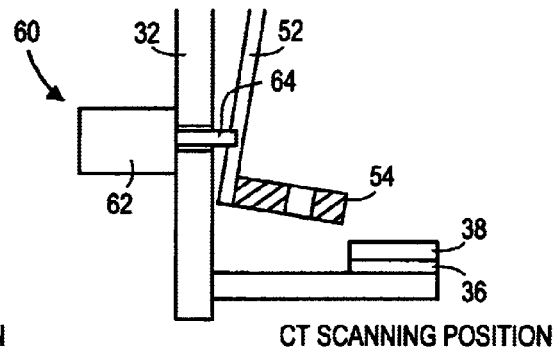
FIG. 6 CT SCANNING POSITION
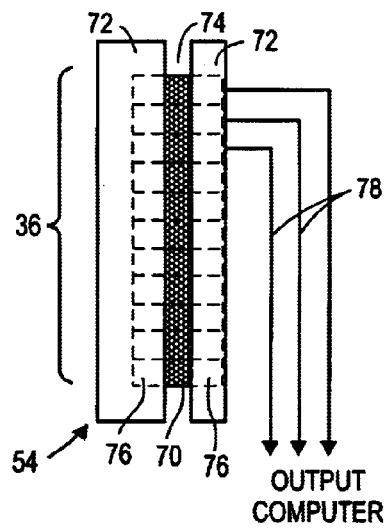
FIG. 5
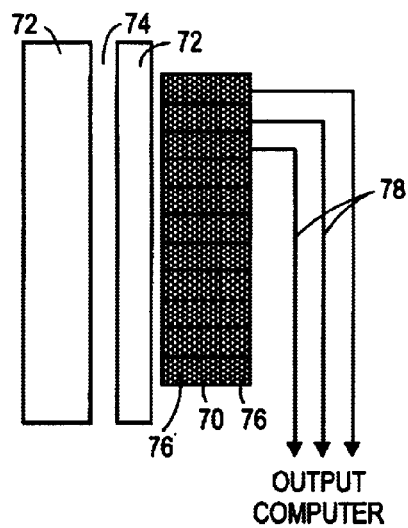
FIG. 7

X-RAY TECHNIQUE-BASED NONINTRUSIVE INSPECTION APPARATUS HAVING AN ADJUSTABLE COLLIMATOR ASSEMBLY

STATEMENT REGARDING FEDERALLY SPONSORED RESEARCH OR DEVELOPMENT

Certain aspects of this invention were developed with support from the FAA (Federal Aviation Association). The U.S. Government may have rights in certain of these inventions.

BACKGROUND OF THE INVENTION

1). Field of the Invention

This invention relates to an x-ray technique-based nonintrusive inspection apparatus, particularly of the kind that may be used for nonintrusively inspecting closed containers before being loaded into a loading bay of an aircraft.

2). Discussion of Related Art

Inspection apparatus are commonly used for nonintrusively inspecting luggage and other closed containers before being loaded into a loading bay of an aircraft. Older generation inspection apparatus relied merely on conventional x-ray technology for nonintrusively inspecting closed containers. More recently, inspection apparatus which rely on computer tomography (CT) scanning technology have also been utilized. An inspection apparatus utilizing CT scanning technology is described in U.S. Pat. Nos. 5,182,764 and 5,367,552 by Peschmann, et al. which are assigned to the assignee of the present case and which are hereby incorporated by reference.

SUMMARY OF THE INVENTION

The invention is for an x-ray-based nonintrusive inspection apparatus. A gantry is rotatably mounted to a support frame, and has an opening through which an object can be transported. A gantry motor is connected to the gantry, and is operable to rotate the gantry. An x-ray source is mounted to the gantry, and a plurality of x-ray detector crystals are mounted to the gantry on a side thereof so that x-rays emitted by the x-ray source radiate through the object before being detected by the x-ray detector crystals. An adjustable collimator is secured to the gantry, and an adjusting actuator is connected to the adjustable collimator. The adjusting actuator is actuable to move the adjustable collimator between a pre-scanning position and a CT scanning position, in the pre-scanning position, the adjustable collimator exposing a smaller portion of a respective crystal to the x-rays than in the CT scanning position. A controller is connected to the gantry motor and the adjusting actuator. The controller controls the motor and the adjusting actuator such that the adjustable collimator is in the pre-scanning position when the gantry is stationary and in the CT scanning position when the gantry is rotating.

According to another aspect of the invention, a conveyor system is secured to a support frame, the conveyor system including at least one conveyor belt to support an object and transfer the object through a gantry opening of a gantry that is rotatably mounted to the support frame. In addition, an adjustable collimator and adjusting actuator are provided to either shield or expose portions of respective x-ray detector crystals.

According to a further aspect of the invention, a method of scanning an object is provided. An adjustable collimator is moved into a pre-scanning position. X-rays are emitted from an x-ray source. The object is moved relative to the x-ray source with the gantry stationary. The x-rays are detected with x-ray detector crystals after the x-rays pass through the object. The adjustable collimator is moved into a CT scanning position. A smaller portion of a respective x-ray detector crystal is exposed by the adjustable collimator when in the pre-scanning position than in the CT scanning position. The x-ray source and the x-ray detector crystals are then rotated around the object while the adjustable collimator is in the CT scanning position.

BRIEF DESCRIPTION OF THE DRAWINGS

The invention is further described by way of example with reference to the accompanying drawings, wherein:

FIG. 4 is an enlarged view of components forming a lower portion of FIG. 2;

FIG. 5 is a top plan view of an adjustable collimator and detector crystals in FIG. 4;

FIG. 6 is an enlarged view of components of FIG. 4;

FIG. 7 is a top plan view of the adjustable collimator and x-ray detector crystals in FIG. 6;

DETAILED DESCRIPTION OF THE INVENTION

Figure 1:
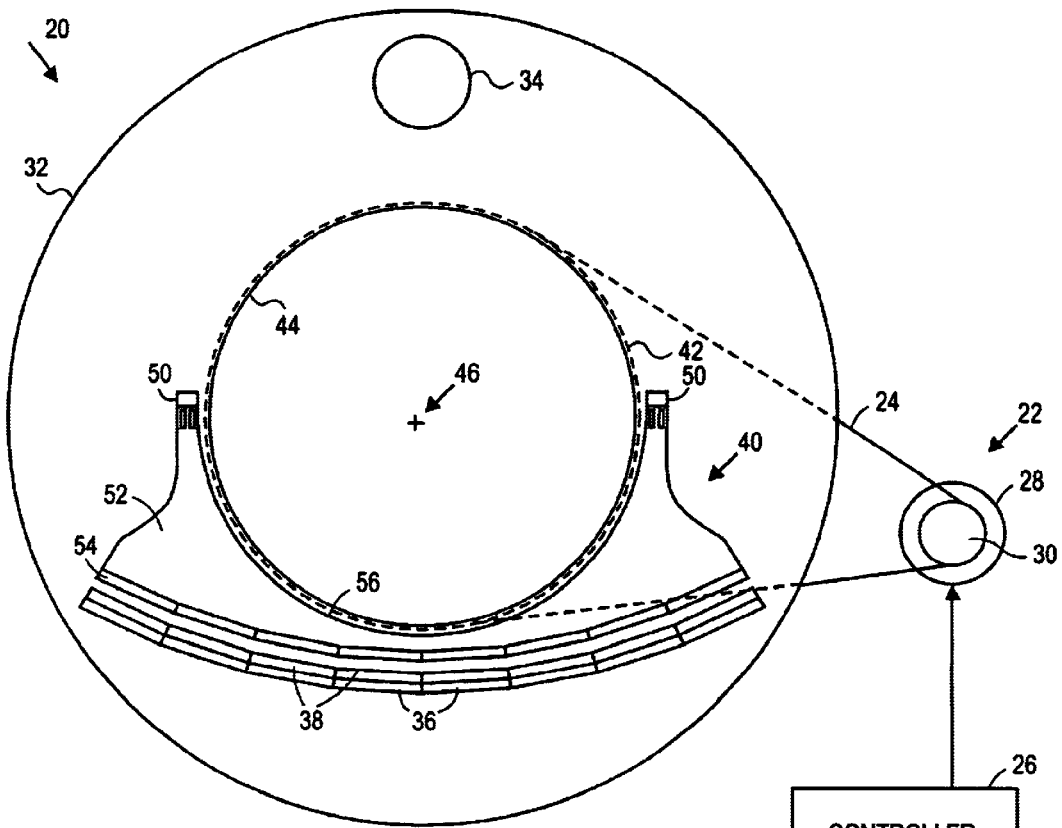
FIG. 1 is an end view, illustrating a gantry assembly and other components of an x-ray-based nonintrusive inspection apparatus according to an embodiment of the invention.

FIG. 1 of the accompanying drawings illustrates subassemblies and components of an x-ray-based nonintrusive inspection apparatus, according to an embodiment of the invention, including a gantry assembly 20, a gantry motor 22, a gantry drive belt 24, and a controller 26.

The gantry motor 22 has a motor body 28 secured to a stationary support frame (not shown), and a pulley 30 rotatably mounted to the motor body 28. The pulley 30 is rotated when power is provided by the controller 26 to the gantry motor 22.

The gantry assembly 20 includes a gantry 32, an x-ray source 34, x-ray detector crystal blocks 36, stationary x-ray detector collimators blocks 38, and an adjustable collimator assembly 40.

The gantry 32 has a small circular outer surface 42 and defines a circular gantry opening 44. The gantry 32 is mounted to the stationary support frame, and is rotatable relative to the stationary support frame about a center axis 46 of the circular outer surface 42 and the gantry opening 44.

The gantry drive belt 24 runs over the pulley 30 and the outer surface 42. The position of the gantry motor 22 is idealized because the gantry motor 22 is actually behind an outer portion of the gantry 32. Rotation of the pulley 30 rotates the gantry 32 about the axis 46.

Figures 2, 3:
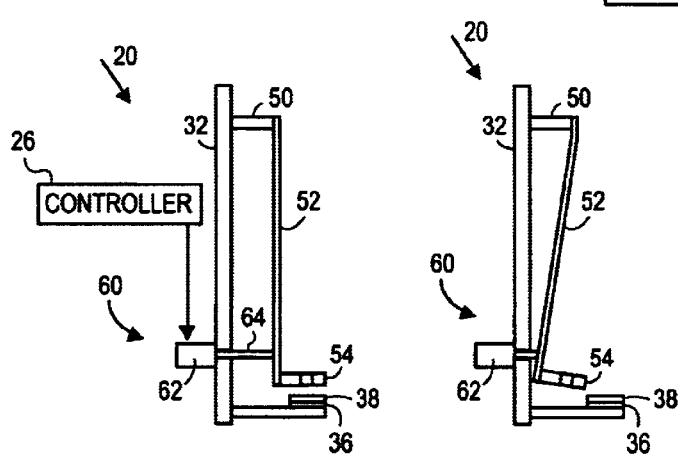
FIG. 2 is a side view of components of the gantry assembly in a pre-scanning position.
FIG. 3 is a view similar to FIG. 2, with the components in a CT scanning position.

Referring now to FIGS. 1, 2, and 3 in combination, the adjustable collimator assembly 40 includes two mounting blocks 50, an flexible plate 52, and a collimator shield 54. The mounting blocks 50 are secured to the gantry 32 on opposing sides of the gantry opening 44. The flexible plate 52 has a curved edge 56 that partially surrounds the gantry opening 44. Upper portions of the flexible plate 52 are secured to the mounting blocks 50, and are spaced from the gantry 32 by the mounting blocks 50. The collimator shield 54 is mounted to a lower edge of the flexible plate 52.

Referring specifically to FIGS. 2 and 3, the adjustable collimator assembly 40 further includes an actuator 60, including an actuator body 62 and an actuating component 64. The actuator body 62 is mounted to the gantry 32 on a side thereof opposing the flexible plate 52. The actuating component 64 extends from the actuator body 62 through an opening in the gantry 32. An end of the actuating component 64 is secured to a lower portion of the flexible plate 52. The controller 26 can provide power to the actuator 60. When power is provided to the actuator 60, the actuating component 64 moves toward the actuator body 62, and bends the flexible plate 52 so that the lower portion thereof moves closer to the gantry 32, as illustrated in FIG. 3.

Referring again to FIG. 1, the x-ray source 34 is secured to the gantry 32 on a side of the gantry opening 44, opposing the collimator shield 54. The collimator shield 54 has a curvature with a center point at the x-ray source 34. The x-ray detector crystal blocks 36 are mounted below the collimator shield 54 to the gantry 32. A curvature formed by the x-ray detector crystal blocks 36 also has a center point at the x-ray source 34. The stationary x-ray detector collimator blocks 38 are secured on the x-ray detector crystal blocks 36, i.e., between the x-ray detector crystal blocks 36 and the collimator shield 54.

FIGS. 4 and 5 illustrate the position of the collimator shield 54 when the flexible plate 52 is not bent and the collimator shield 54 is in a pre-scanning position. Each x-ray detector crystal block 36 has a plurality of x-ray detector crystals 70. Each respective x-ray detector crystal 70 is connected through a respective output line 78 to an output computer. Each x-ray detector crystal 70 has a length which is longer than its width, and the x-ray detector crystals 70 are located side-by-side to form a respective x-ray detector crystal block 36. The collimator shield 54 has two elongated portions 72 defining an elongated slit 74 therebetween. The elongated portions 72 are made of a material that substantially attenuates x-ray radiation, such as molybdenum. When the collimator shield 54 is in the pre-scanning position as illustrated in FIGS. 4 and 5, the elongated portions 72 are positioned over end portions 76 of each respective x-ray detector crystal 70. Only a small central portion of each x-ray detector crystal 70 is exposed through the elongated slit 74. Only the central portions of the x-ray detector crystals 70 are exposed to x-rays from the x-ray source (34 in FIG. 1).

FIGS. 6 and 7 illustrate the collimator shield 54 in a CT scanning position, i.e., with the flexible plate 52 bent toward the gantry 32. The collimator shield 54 is entirely moved off the x-ray detector crystals 70 so that the entire length of each x-ray detector crystal 70 is exposed to x-rays from the x-ray source.

Figure 8:
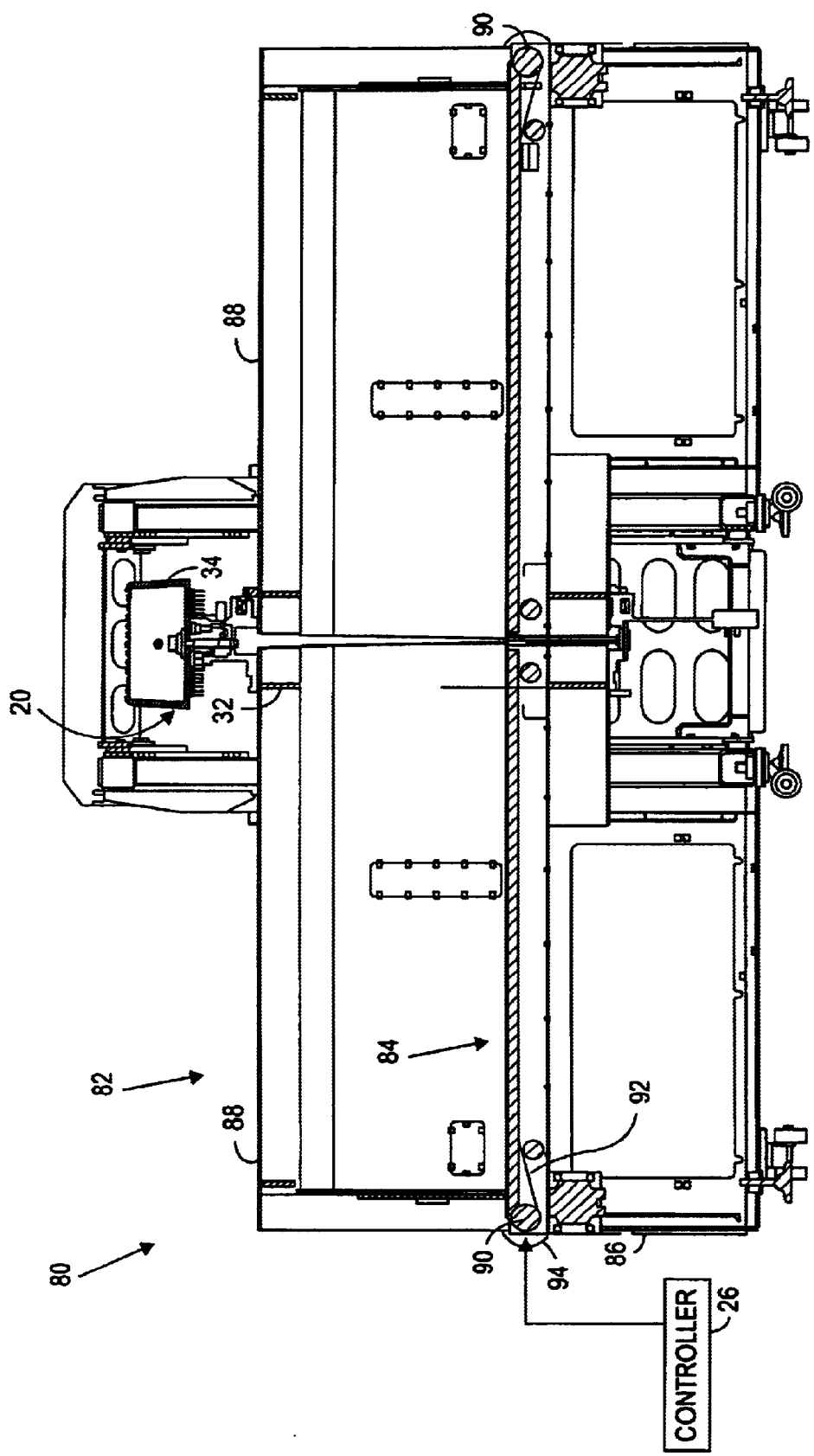
FIG. 8 is a cross-sectional side view of an x-ray-based nonintrusive inspection apparatus.

FIG. 8 illustrates the x-ray-based nonintrusive inspection apparatus 80, which includes a stationary support frame 82 hereinbefore mentioned, a conveyor system 84, and the gantry assembly 20 hereinbefore described.

The support frame 82 includes a base frame 86 and two tunnel portions 88 mounted on the base frame 86. The gantry 32 is rotatably mounted to one of the tunnel portions 88.

The conveyor system 84 includes two conveyor rollers 90 on opposing sides of the base frame 86 and a conveyor belt 92 that runs over the conveyor rollers 90 and forms a closed loop. A conveyor motor 94 is mounted to the base frame 86. The controller 26 can provide power to the conveyor motor 94, so that the conveyor motor 94 rotates one of the conveyor rollers 90. An object can be placed on the conveyor belt 92 at one end of the base frame 86 and be transported on the conveyor belt 92 through one of the tunnel portions 88, the gantry assembly 20, and then through the other one of the tunnel portions 88.

Figure 9:
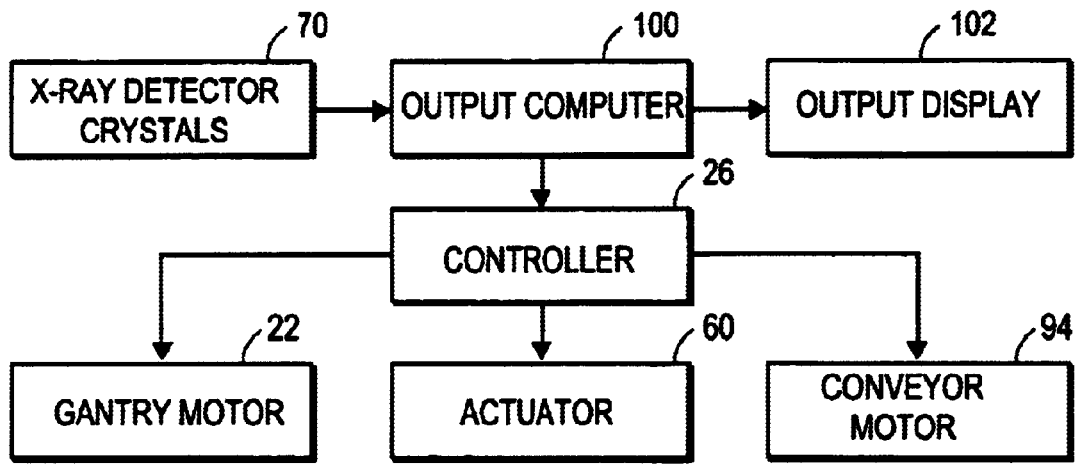
FIG. 9 is a block diagram of components that are used for controlling and moving various parts of the x-ray-based nonintrusive inspection apparatus.

As illustrated in FIG. 9, the x-ray detector crystals 70 are connected to an output computer 100. The output computer 100 analyzes signals, received from the x-ray detector crystals 70, indicating the intensity of x-rays that are detected by the x-ray detector crystals 70. An output display 102 is connected to the output computer, and can provide a visual representation indicative of the intensities of x-rays detected by each x-ray detector crystal 70. The controller 26 is connected to the output computer 100. The gantry motor 22, actuator 60, and conveyor motor 94 are all connected to the controller 26 and are under the control of the controller 26. The output computer 100 and the controller 26 are typically computers, each having a processor and memory coupled to the processor. A software program can be stored in the memory. The software program has a set of commands that are executable by the respective processor. The set of instructions should be evident from the description that follows.

Figure 10:
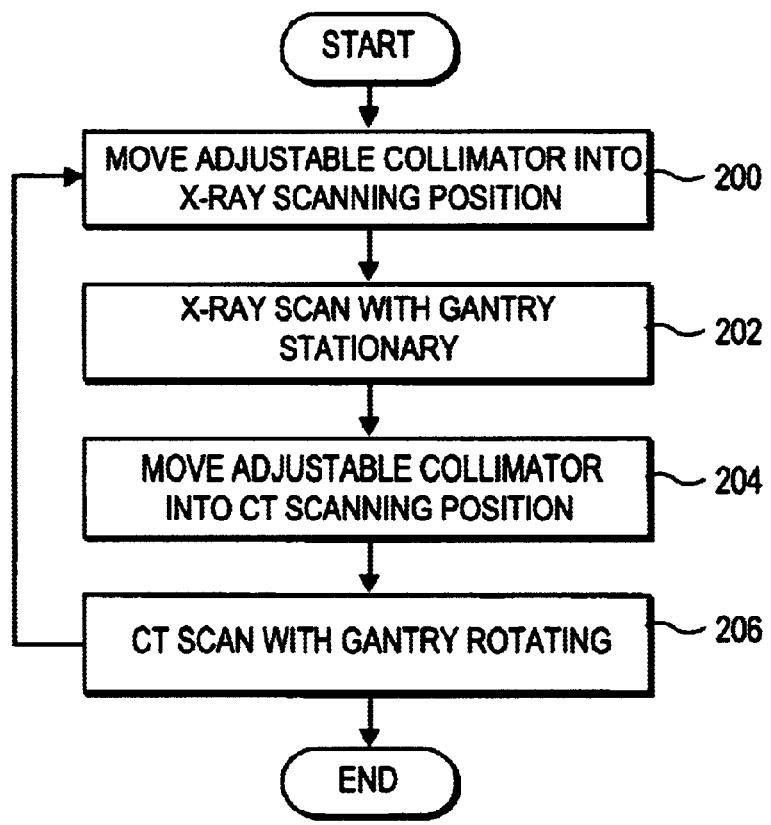
FIG. 10 is a flow chart illustrating the basic operation of the x-ray-based nonintrusive inspection apparatus.

FIG. 10 is a basic representation of how the inspection apparatus is used to scan a luggage container. The collimator shield 54 is first moved into the pre-scanning position illustrated in FIGS. 2, 4, and 5 (Step 200). An x-ray scan is then executed with the gantry assembly 20 in a stationary position relative to the support frame 82 (Step 202). With the x-ray source 34 at the bottom, opposite to the orientation illustrated in FIG. 1, the container is transported on the conveyor belt 92 at a fixed, predetermined speed. X-rays emitted by the x-ray source 34 radiate through the container and are detected by the x-ray detector crystals 70. The output computer 100 reads a signal from each x-ray detector crystal 70 at fixed intervals. An image with higher resolution in the direction of belt travel can be generated because a relatively small portion of each x-ray detector crystal 70 is exposed when the collimator shield 54 is in the pre-scanning position, yielding spatially closer independent readouts of the x-ray detector data.

X-ray scanning with the collimator shield 54 in the pre-scanning position is continued until an image of the entire container is acquired. The output computer 100 then determines if there is an object or objects in the container that requires a more accurate analysis with a CT scan. The collimator shield 54 is then moved into the CT scanning position of FIGS. 3, 6, and 7 (Step 204) while the gantry motor 22 rotates the gantry assembly 20 at a constant predetermined speed. The output computer 100 then moves the container such that the CT plane intersects the object identified during the x-ray scan. A CT scan is then initiated (Step 206) to create a cross-sectional image of the identified object. The container is then transported back through the gantry assembly 20 to carry out subsequent CT scans on other objects identified in the x-ray scan. Each CT scan is composed of a series of one-dimensional x-ray data (referred to as views) taken from subsequent angular positions of the gantry assembly 20. CT views are obtained sequentially at a predetermined fractional degree of rotation of the gantry assembly (20) while the gantry is rotating at a constant speed. Because the views must be obtained with the gantry assembly 20 at speed, the exposure time (referred to as integration time) per view is very short. The full crystal length is exposed to the x-ray beam during a CT scan to increase the signal to noise ratio over the limited integration time. Although the longer crystal reduces the spatial resolution in the dimension of container travel, the CT scan is specific to a planar section perpendicular to the belt and has lower sensitivity to objects that do not exist within the CT plane.

When CT scanning is completed, the collimator shield 54 is again returned to the pre-scanning position (Step 200), and subsequent containers are scanned (Step 202).

It can thus be seen that the collimator shield 54 allows for relatively accurate x-ray scanning and subsequent CT scanning utilizing the same x-ray source 34, while signal to noise ratio in a given time period remains comparatively high. The flexible plate 52 provides a convenient mounting and adjustment mechanism for the collimator shield 54 with the collimator shield 54 having a center point at the x-ray source 34, while still allowing for a container to be transported through the gantry opening 44.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed is:

1. An x-ray-based nonintrusive inspection apparatus, comprising:
   a support frame;
   a gantry rotatably mounted to the support frame, the gantry having an opening through which an object can be transported;
   a gantry motor connected to the gantry, and being operable to rotate the gantry;
   an x-ray source mounted to the gantry;
   a plurality of x-ray detector crystals mounted to the gantry on a side thereof so that x-rays emitted by the x-ray source radiate through the object before being detected by the x-ray detector crystals;
   a collimator shield secured to the gantry;
   an adjusting actuator connected to the collimator shield and being actuable to move the collimator shield between a pre-scanning position and a CT scanning position, in the pre-scanning position the collimator shield exposing a smaller portion of a respective crystal to the x-rays than in the CT scanning position; and
   a controller connected to the gantry motor and the adjusting actuator and controlling the motor and adjusting actuator such that the collimator shield is in the pre-scanning position when the gantry is stationary and in the CT scanning position when the gantry is rotating.

2. The x-ray-based nonintrusive inspection apparatus of claim 1, further comprising:
   a conveyor system secured to the frame, the conveyor system including at least one conveyor belt to support the object and transfer the object through a plane between the x-ray source and the x-ray detector crystals.

3. The x-ray-based nonintrusive inspection apparatus of claim 1, wherein each x-ray detector crystal is elongated in a direction in which the object travels and the collimator shield moves in a direction in which the object travels.

4. The x-ray-based nonintrusive inspection apparatus of claim 3, wherein the collimator shield defines a slit through which a central region of the respective x-ray detector crystal is exposed while portions of the collimator shield opposing end regions of the respective crystal.

5. The x-ray-based nonintrusive inspection apparatus of claim 1, further comprising:
   a gantry drive belt, the gantry motor driving the gantry drive belt and the gantry drive belt rotating the gantry.

6. The x-ray-based nonintrusive inspection apparatus of claim 1, further comprising:
   a flexible plate having one portion secured to the gantry and the collimator shield being secured to another portion of the flexible plate, the flexible plate bending to allow for movement of the collimator shield.

7. The x-ray-based nonintrusive inspection apparatus of claim 6, wherein the flexible plate bends when the collimator shield moves from the pre-scanning position into the CT scanning position.

8. The x-ray-based nonintrusive inspection apparatus of claim 6, wherein the flexible plate partially surrounds the gantry opening and bends at two locations on opposing sides of the gantry opening.

9. The x-ray-based nonintrusive inspection apparatus of claim 1, further comprising:
   a display computer connected to the x-ray detector crystals; and
   a display screen connected to the display computer and providing a visual output based upon the strength of x-rays detected by the x-ray detector crystals.

10. The x-ray-based nonintrusive inspection apparatus of claim 1, further comprising:
    an x-ray detector collimator mounted over the x-ray detector crystals in a stationary position relative to the x-ray detector crystals, the x-ray detector collimator having a plurality of septa with a plurality of septa gaps therebetween.

11. The x-ray-based nonintrusive inspection apparatus of claim 10, wherein the x-ray detector collimator is between the collimator shield and the x-ray detector crystals when the collimator shield is in the pre-scanning position.

12. An x-ray-based nonintrusive inspection apparatus, comprising:
    a support frame;
    a gantry rotatably mounted to the support frame, the gantry having an opening through which an object can be transferred;
    a conveyor system secured to the frame, the conveyor system including at least one conveyor belt to support the object and transfer the object through the gantry opening;
    an x-ray source mounted to the gantry;
    a plurality of x-ray detector crystals mounted to the gantry on a side thereof so that x-rays emitted by the x-ray source radiate through the object before being detected by the x-ray detector crystals;
    a collimator shield secured to the gantry; and
    an adjusting actuator connected to the collimator shield and being actuable to move the collimator shield between a pre-scanning position and a CT scanning position, in the pre-scanning position the collimator shield exposing a smaller portion of a respective crystal to the x-rays than in the CT scanning position.

13. The x-ray-based nonintrusive inspection apparatus of claim 12, wherein the conveyor belt transfers the object through a plane between the x-ray source and the x-ray detector crystals.

14. An x-ray-based nonintrusive inspection apparatus, comprising:

a support frame;

a gantry rotatably mounted to the support frame, the gantry having a gantry opening;

at least two conveyor rollers, each being rotatably mounted to the support frame;

a conveyor belt forming a closed loop and running over the conveyor rollers, the conveyor belt being capable of supporting an object;

a conveyor belt motor secured to the support frame and connected to the conveyor belt to run the conveyor belt over the conveyor belt rollers and transport the object across the support frame;

a gantry motor connected to the gantry to rotate the gantry relative to the support frame;

an x-ray source mounted to the gantry;

a plurality of x-ray detector crystals mounted to the gantry on a side thereof so that x-rays emitted by the x-ray source radiate through the object before being detected by the x-ray detector crystals;

a collimator shield secured to the gantry; and an adjusting actuator connected to the collimator shield and being actuable to move the collimator shield between a pre-scanning position and a CT scanning position, in the pre-scanning position the collimator shield exposing a smaller portion of a respective crystal to the x-rays than in the CT scanning position.

15. The x-ray-based nonintrusive inspection apparatus of claim 14, further comprising:

a controller connected to the gantry motor and the adjusting actuator and controlling the motor and adjusting actuator such that the collimator shield is in the pre-scanning position when the gantry is stationary and in the CT scanning position when the gantry is rotating.

16. A method of scanning an object, comprising:

moving a collimator shield into a pre-scanning position;

emitting x-rays from an x-ray source;

moving an object through relative to the x-ray source;

detecting the x-rays with x-ray detector crystals after the x-rays pass through the object;

moving the collimator shield into a CT scanning position, a smaller portion of a respective x-ray detector crystal being exposed by the collimator shield when in the pre-scanning position than in the CT scanning position; and rotating the x-ray source and the x-ray detector crystals around the object while the collimator shield is in the CT scanning position.

17. The method of claim 16, wherein the x-ray source and x-ray detector crystals do not rotate about the object when the collimator shield is in the x-ray scanning mode.

* * * * *